(12) United States Patent
Wada et al.

(10) Patent No.: US 8,565,852 B2
(45) Date of Patent: Oct. 22, 2013

(54) AURICLE-INSTALLED DEVICE AND BIO-SIGNAL MEASUREMENT APPARATUS

(75) Inventors: Seija Wada, Kanagawa (JP); Takuro Yamamoto, Kanagawa (JP); Shiko Yamashita, Tokyo (JP); Yusaku Nakashima, Tokyo (JP)

(73) Assignee: Sony Corporation, Tokyo (JP)

( * ) Notice: Subject to any disclaimer, the term of this patent is extended or adjusted under 35 U.S.C. 154(b) by 440 days.

(21) Appl. No.: 12/818,415

(22) Filed: Jun. 18, 2010

(65) Prior Publication Data

US 2010/0331660 A1 Dec. 30, 2010

(30) Foreign Application Priority Data

Jun. 29, 2009 (JP) .................. P2009-153984

(51) Int. Cl.
*A61B 5/0478* (2006.01)
*A61B 5/0492* (2006.01)
*A61B 5/0496* (2006.01)

(52) U.S. Cl.
USPC .......................................... 600/379; 600/383

(58) Field of Classification Search
USPC .................................................. 600/379, 383
See application file for complete search history.

(56) References Cited

U.S. PATENT DOCUMENTS

| 4,601,294 | A  | * | 7/1986  | Danby et al. ............ 600/379 |
| 7,797,042 | B2 | * | 9/2010  | Dietrich et al. .............. 607/2 |
| 7,856,275 | B1 | * | 12/2010 | Paul et al. ................ 607/55 |
| 8,137,286 | B2 | * | 3/2012  | Nakatomi et al. .......... 600/559 |
| 2006/0094974 | A1 | * | 5/2006  | Cain ........................ 600/544 |
| 2008/0165017 | A1 | * | 7/2008  | Schwartz ................ 340/573.1 |
| 2011/0004089 | A1 | * | 1/2011  | Chou ....................... 600/383 |

FOREIGN PATENT DOCUMENTS

| JP | 2001-353130 | 12/2001 |
| JP | 2008-67911  | 3/2008  |

* cited by examiner

*Primary Examiner* — Lee S Cohen
(74) *Attorney, Agent, or Firm* — K&L Gates LLP

(57) ABSTRACT

Disclosed herein is an auricle-installed device including, a reference electrode to be placed on the ear lobe, a detection electrode to be placed on a surface exposed to bones surrounding the auricle of the ear, and a support body for supporting the reference and detection electrodes.

2 Claims, 11 Drawing Sheets

FIG. 8
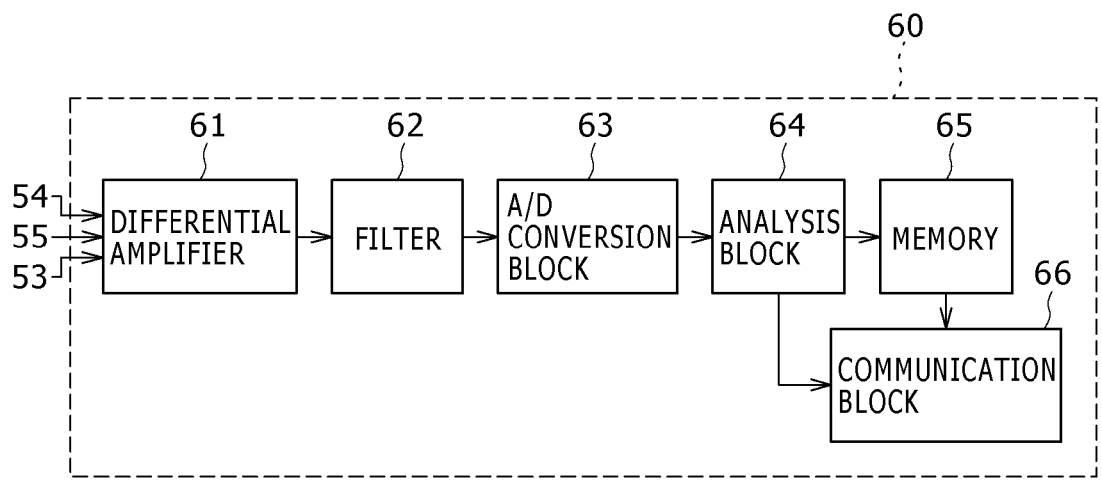
FIG.9A  FIG.9B
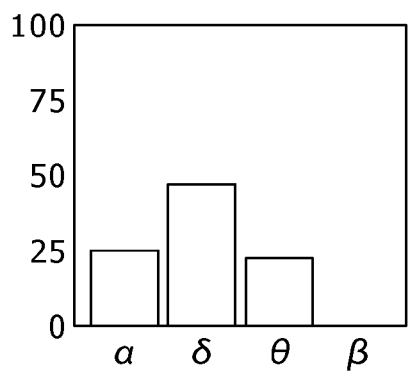
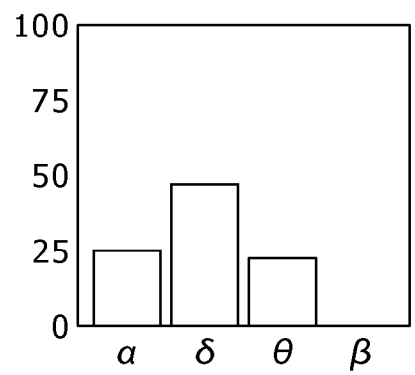

AURICLE-INSTALLED DEVICE AND BIO-SIGNAL MEASUREMENT APPARATUS

CROSS REFERENCES TO RELATED APPLICATIONS

The present application claims priority to Japanese Priority Patent Application JP 2009-153984 filed in the Japan Patent Office on Jun. 29, 2009, the entire content of which is hereby incorporated by reference.

BACKGROUND

In general, the present application relates to an auricle-installed device and a bio-signal measurement apparatus employing the auricle-installed device. For example, the present application is well applied to devices and apparatus in typically a field in which waves generated in a biological body and propagated through the biological body are acquired as an electrical signal.

The conventional apparatus hitherto known for acquiring bio-signals such as brain waves typically employs a head gear which has a number of electrodes. The numerous electrodes of the head gear are brought into contact with the head of a medical examinee by mounting the head gear on the head of the medical examinee. Then, from the numerous electrodes, the known bio-signal acquisition apparatus acquires electrical signals each representing a bio-signal which is generated in and propagated through the biological body of the examinee.

As described above, the numerous electrodes of the known bio-signal acquisition apparatus must be brought into contact with the head of a medical examinee by mounting the head gear of the apparatus on the head of the medical examinee. Thus, not only does the medical-examination work become complicated, but the medical examinee is also placed under restrain of having the numerous electrodes brought into contact with the head of the medical examinee for long time. As a result, since the numerous electrodes brought into contact with the head of the medical examinee for long time, this could be a burden for the medical examinee, and making the examinee feels uncomfortable.

In order to solve the problem described above, an external auditory meatus electrode unit has been proposed in Japanese Patent Laid-open No. 2008-67911 for fetching brain waves or the like by making use of a spring-shaped electrode which is inserted into an external auditory meatus of the medical examinee.

SUMMARY

By the way, since the external auditory meatus electrode unit cited above is a unit to be inserted into an external auditory meatus of a medical examinee, the unit must be designed to have a size which allows the unit to be placed at a location with an area narrower than the inner diameter of the external auditory meatus. Thus, when the electrode having a spring shape is inserted into the external auditory meatus of a medical examinee, a gap is formed between the electrode having a spring shape and the external auditory meatus. As a result, the gap inevitably serves as a cause of extremely worsening the sensitivity of a process to fetch an electrical signal which represents waves propagated through the biological body of the medical examinee.

In addition, on the back side of the external auditory meatus, nerves are concentrated. Thus, in the case of an electrode inserted into the external auditory meatus, it is quite normal to assume a case in which the electrode brought into contact with a pillow during typically a sleep time is further inserted by the pillow toward the back side of the external auditory meatus, damaging the nerves, when the medical examinee rolls over in bed.

Addressing the problems described above, inventors have innovated an auricle-installed device capable of better assuring safety of the medical examinee while sustaining the sensitivity of the measurement of bio-signals at a certain level and innovated a bio-signal measurement apparatus which employs the auricle-installed device.

In order to solve the problems described above, the inventors have innovated an auricle-installed device (such as an auricle-installed device shown in diagrams of FIGS. 1A and 1B) which employs a reference electrode (such as a reference electrode 3) to be placed on the ear lobe, a detection electrode (such as a detection electrode 6) to be placed on a surface exposed to bones surrounding the auricle as well as a support body (such as a support plate 2) for supporting the reference and detection electrodes.

Also in order to solve the problems described above, the inventors have innovated a bio-signal measurement apparatus which employs the auricle-installed device explained above and an amplifier for amplifying a difference in electric potential between the reference and detection electrodes as a bio-signal. The amplifier is included in a signal processing section embedded inside the support body cited above. As described above, the auricle-installed device employs a reference electrode to be placed on the ear lobe, a detection electrode to be placed on a surface exposed to bones surrounding the auricle as well as a support body for supporting the reference and detection electrodes.

When the auricle-installed device having a configuration explained above is installed on the auricle of an ear of a medical examinee, the reference electrode of the auricle-installed device is placed on the ear lobe whereas the detection electrode of the auricle-installed device is placed on a surface exposed to bones surrounding the auricle. Thus, waves generated in the biological body of the examinee and propagated through the biological body can be acquired as a bio-signal directly without the need for the waves to propagate through an air layer. In addition, since the detection electrode of the auricle-installed device is placed on a surface exposed to bones surrounding the auricle, the safety of the medical examinee can also be assured better.

As described above, in accordance with the present application, when the auricle-installed device having a configuration described above is installed on the auricle of an ear of a medical examinee, the reference electrode of the auricle-installed device is placed on the ear lobe whereas the detection electrode of the auricle-installed device is placed on a surface exposed to bones surrounding the auricle. Thus, waves generated in the biological body of the examinee and propagated through the biological body can be acquired as a bio-signal directly without the need for the waves to propagate through an air layer. In addition, since the detection electrode of the auricle-installed device is placed on a surface exposed to bones surrounding the auricle, the safety of the medical examinee can also be assured better. As a result, the auricle-installed device and the bio-signal measurement apparatus employing the auricle-installed device are capable of better assuring the safety of the medical examinee while sustaining the sensitivity of the measurement of bio-signals at a certain level.

Additional features and advantages are described herein, and will be apparent from the following Detailed Description and the figures.

BRIEF DESCRIPTION OF THE FIGURES

FIG. 8 is a circuit diagram showing the circuit configuration of a signal processing section employed in the bio-signal measurement apparatus according to the second embodiment;

FIG. 9A is a diagram showing typical results of the brain-wave measurements according to the second embodiment;

FIG. 9B is a diagram showing other typical results of the brain-wave measurements according to the second embodiment carried out for a comparison purpose;

DETAILED DESCRIPTION

Figure 1A:
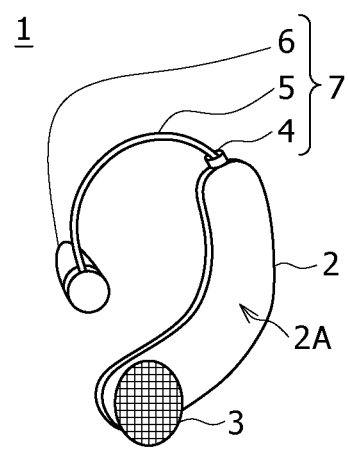
FIG. 1A is a diagram roughly showing the bio-signal measurement apparatus according to a first embodiment as seen from a position on a specific side of the apparatus.
Figure 1B:
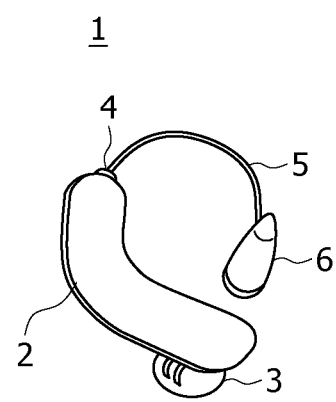
FIG. 1B is a diagram roughly showing the bio-signal measurement apparatus according to the first embodiment as seen from a position on a side opposite to the specific side of the apparatus.

The present application will be described in detail below with reference to the drawings according to an embodiment.
1: First Embodiment
2: Second Embodiment
3: Third Embodiment
4: Other Embodiments
1: First Embodiment
1-1: Configuration of a Bio-Signal Measurement Apparatus As shown in FIGS. 1A and 1B, the bio-signal measurement apparatus 1 employs a support plate 2 formed to fit the base of an auricle of a medical examinee, a reference electrode 3 to be placed on the lobe, a connector 4, a main-spring rod 5 which can be hooked on the auricle and a detection electrode 6.

The support plate 2 is made from typically a plastic material. The support plate 2 is designed to have a shape resembling a bow that is formed to fit the base of the auricle. The support plate 2 is created into such a form that, when the bio-signal measurement apparatus 1 is installed on the auricle of a medical examinee, a specific one of the two ends of the support plate 2 is placed at a location in close proximity to the ear lobe.

Figure 2:
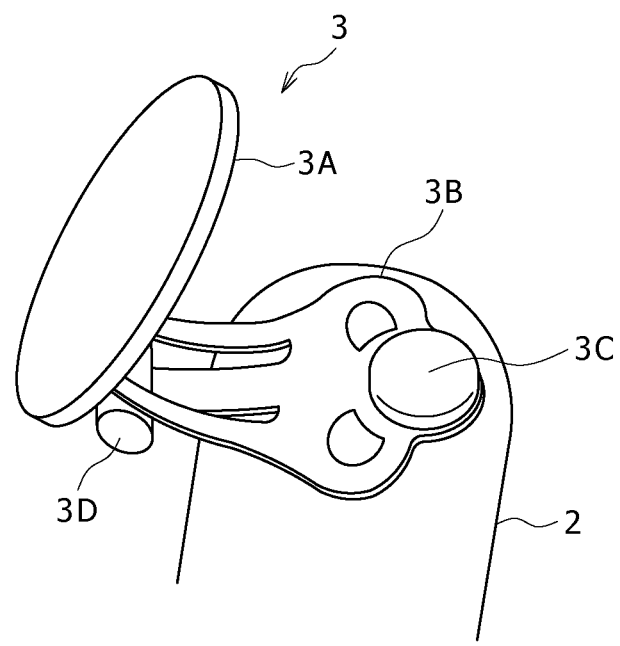
FIG. 2 is a diagram roughly showing the configuration of a reference electrode employed in the bio-signal measurement apparatus according to the first embodiment.

The reference electrode 3 is attached to the surface 2A of the specific end of the support plate 2. The reference electrode 3 is a conductor which is made from typically a metallic material. FIG. 2 is a diagram roughly showing the configuration of the reference electrode 3. As shown in this figure, a stud 3C of the reference electrode 3 is used for fixing the specific end of the support plate 2 and a specific one of the two ends of a clip 3B of the reference electrode 3 to each other.

The reference electrode 3 also has an electrode plate 3A provided on the other end of the clip 3B. The electrode plate 3A is provided on the other end of the clip 3B through a link section 3D which is attached to the other end of the clip 3B. The electrode plate 3A has a shape resembling a coin which has about the same surface area as an ear lobe. Thus, the electrode plate 3A is linked to the support plate 2 in such a state that, with the link section 3D used as a support point, the electrode plate 3A can be rotated in a direction departing from the support plate 2 or a direction approaching the support plate 2.

As shown in the diagrams of FIG. 1, the other end of the support plate 2 is connected by the connector 4 to the main spring rod 5. The connector 4, the main spring rod 5 and the detection electrode 6 form a detection unit 7. The detection electrode 6 is made of typically a conductive plastic material. The detection unit 7 can be attached to the support plate 2 and taken away from the support plate 2 with a high degree of freedom.

Figure 3:
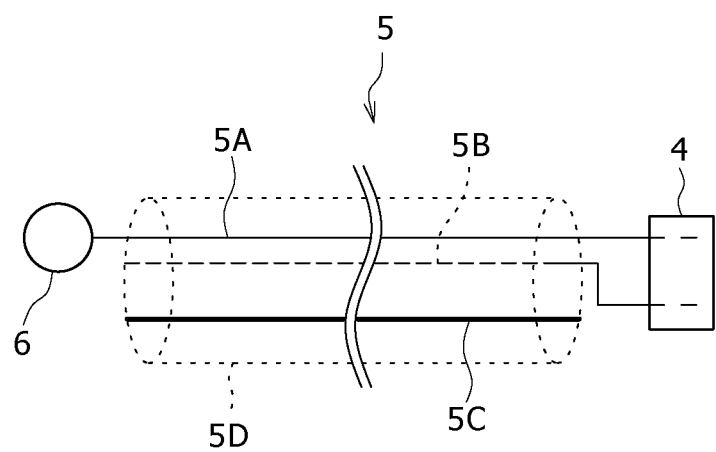
FIG. 3 is a diagram roughly showing the configuration of a main spring rod employed in the bio-signal measurement apparatus according to the first embodiment.

As shown in FIG. 3, the main spring rod 5 is configured to employ a signal wire 5A, a shield 5B, a wire-like spring 5C and a tube 5D which covers the signal wire 5A, the shield 5B and the wire-like spring 5C. The tube 5D is made from an elastic material such as rubber. A specific one of the two ends of the signal wire 5A is connected to the detection electrode 6 whereas the other end of the signal wire 5A is connected to the connector 4.

The shield 5B is made from a metallic material. The shield 5B has a shape resembling a net which covers the signal wire 5A. The shield 5B shields the signal wire 5A against incoming noises such as electrical waves. A specific one of the two ends of the shield 5B is connected to the ground through the connector 4.

The wire-like spring 5C is formed into a shape resembling a circular arc. The entire main spring rod 5 is thus created to have a form adjusted to the shape resembling a circular arc. If an external force determined in advance is applied to the wire-like spring 5C, the wire-like spring 5C generates a reactionary force for making an attempt to restore the wire-like spring 5C to the original shape resembling a circular arc.

As described above, the signal wire 5A employed in the main spring rod 5 connects the connector 4 to the detection electrode 6 and is shielded by the shield 5B against noises generated by external sources. In addition, the wire-like spring 5C generates a reactionary force against an external force applied to the main spring rod 5 in order to continuously sustain the wire-like spring 5C at the original shape resembling a circular arc.

A specific one of the two ends of the detection electrode 6 has a shape approximately resembling a round cone. The bio-signal measurement apparatus 1 is created into such a configuration that, when the bio-signal measurement apparatus 1 is installed onto the auricle of a medical examinee, the aforementioned specific end of the detection electrode 6 employed in the bio-signal measurement apparatus 1 is engaged with the area between the crus of helix and the superior crux of antihelix. In addition, the detection electrode 6 is designed into such a shape that, when the specific end of the detection electrode 6 is engaged with the area between the superior crux and the inferior crux of the auricle, the conical surface of the specific end of the detection electrode 6 is brought into contact with the surface of the area which is also referred to hereafter as an ear pocket.

Inside the support plate 2, there is provided a signal processing section 30 which is not shown in the diagrams of FIGS. 1A to 3. The signal processing section is connected to the reference electrode 3. In addition, the signal processing section 30 is also connected to the detection electrode 6 through the connector 4 and the signal wire 5A.

By the way, in order to mount the bio-signal measurement apparatus 1 on the auricle of an ear of a medical examinee, first of all, the main spring rod 5 is stretched so that the detection electrode 6 is separated away from the support plate 2. Then, the support plate 2 is brought into contact with the base of the auricle so that an end of the support plate 2 is placed at a location in close proximity to the ear lobe. In addition, the main spring rod 5 is brought into contact with an auricle-base upper-side portion exposed to the scaphoid fossa.

Subsequently, the reference electrode 3 is held firmly by having the ear lobe sandwiched between the electrode plate 3A and the stud 3C which is provided on the clip 3B as shown in the diagram of FIG. 3. In this state, the reference electrode 3 is held firmly by bringing the electrode plate 3A, the clip 3B and the stud 3C into contact with the ear lobe. Thus, the electrode plate 3A, the clip 3B and the stud 3C function as an electrode. It is to be noted that the electrode plate 3A has a shape resembling a coin which has about the same surface area as an ear lobe as described earlier. It is thus easy for the medical examinee to carry the bio-signal measurement apparatus 1 by sandwiching the ear lobe between the electrode plate 3A and the stud 3C which is provided on the clip 3B.

On the other hand, the bio-signal measurement apparatus 1 is installed onto the auricle of an ear by placing a specific one of the two ends of the detection electrode 6 at such a position that its specific end is brought into contact with the ear pocket. With the detection electrode 6 inserted into the ear pocket, a force generated by the main spring rod 5 is pushing the support plate 2 toward the base of the auricle.

Figure 4A:
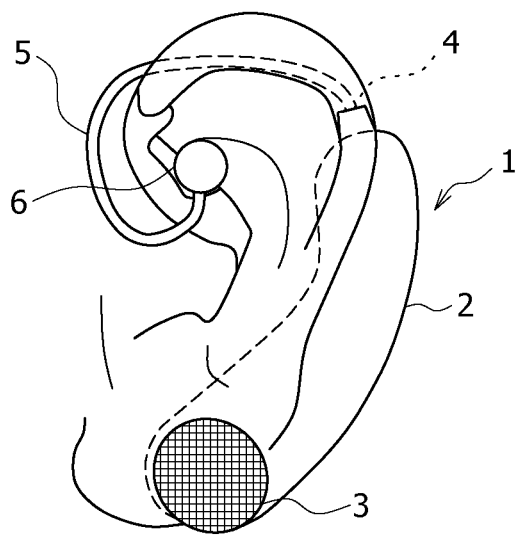
FIG. 4A is a diagram roughly showing a mounting state in which the reference electrode employed in the bio-signal measurement apparatus according to the first embodiment is firmly held on an ear lobe.

As shown in the diagram of FIG. 4A, the reference electrode 3 is held firmly on the ear lobe, the main spring rod 5 is brought into contact with the upper-side portion of the base of the auricle whereas the detection electrode 6 is engaged with the ear pocket. Thus, the bio-signal measurement apparatus 1 is held firmly on an ear of the medical examinee at 3 support points.

The main spring rod 5 is designed so that, with the bio-signal measurement apparatus 1 installed on an auricle of the medical examinee, the main spring rod 5 generates a force working in a direction to drive the support plate 2 and the detection electrode 6 to mutually approach each other. With the bio-signal measurement apparatus 1 installed on the auricle, the support plate 2 is held firmly on the base of the auricle by the force generated by the main spring rod 5 to push the support plate 2 against the base of the auricle. Thus, it is possible to prevent the bio-signal measurement apparatus 1 from falling off from the ear of the medical examinee.

By designing the main spring rod 5 as described above, it becomes easy for the medical examinee to mount the bio-signal measurement apparatus 1 on an auricle of the medical examinee or move the bio-signal measurement apparatus 1 from the auricle. Every individual medical examinee has a unique auricle shape and auricle-shape variations from examinee to examinee give rise to variations in ear pocket position from examinee to examinee. However, the bio-signal measurement apparatus 1 is capable of keeping up with variations in ear pocket position from examinee to examinee.

Figure 4B:
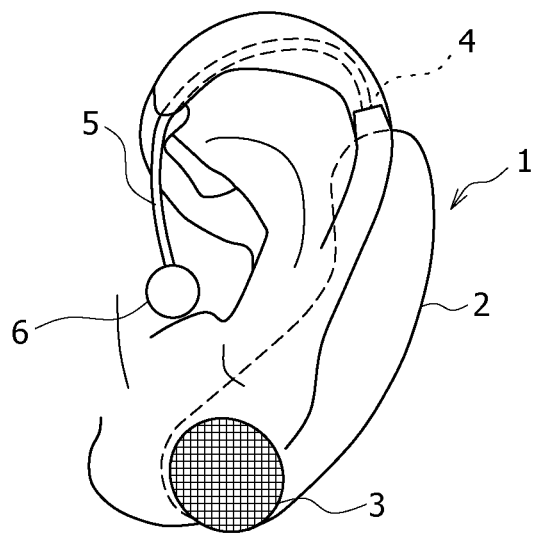
FIG. 4B is a diagram roughly showing a mounting state in which the detection electrode employed in the bio-signal measurement apparatus according to the first embodiment can be inserted into an external auditory meatus.

By the way, not only does the bio-signal measurement apparatus 1 allow the detection electrode 6 to be held firmly in the ear pocket as shown in the diagram of FIG. 4A but, by deforming the main spring rod 5, the bio-signal measurement apparatus 1 also allows the detection electrode 6 to be inserted into the external auditory meatus as shown in the diagram of FIG. 4B. Also in the case of the bio-signal measurement apparatus 1 shown in the diagram of FIG. 4B, the force generated by the main spring rod 5 firmly holds the bio-signal measurement apparatus 1 by pushing the support plate 2 against the base of the auricle. Thus, it is possible to prevent the bio-signal measurement apparatus 1 from falling off from the ear of the medical examinee.

1-2: Configuration of the Signal Processing Apparatus

Figure 5:
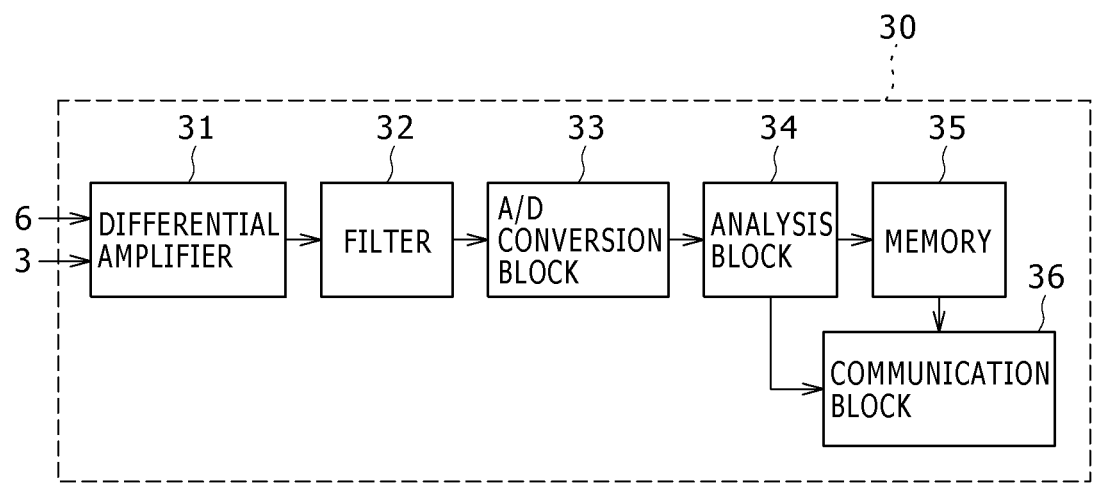
FIG. 5 is a circuit diagram showing the circuit configuration of a signal processing section employed in the bio-signal measurement apparatus according to the first embodiment.

In FIG. 5, the signal processing section 30 is provided inside the support plate 2. As shown in the figure, the signal processing section 30 is configured to employ a differential amplifier 31, a filter 32, an A/D (Analog-to-Digital) conversion section 33, an analysis block 34, a memory 35 and a communication block 36.

When an operation section employed in the support plate 2 issues a command to start a measurement to the signal processing section 30, the signal processing section 30 provides a voltage generated by a power supply such as a battery to the differential amplifier 31, the filter 32, the A/D conversion block 33, the analysis block 34, the memory 35 and the communication block 36. When the operation section issues a command to stop the measurement to the signal processing section 30, on the other hand, the signal processing section 30 terminates the operation to provide the voltage generated by the power supply to the differential amplifier 31, the filter 32, the A/D conversion block 33, the analysis block 34, the memory 35 and the communication block 36.

The differential amplifier 31 is a section for amplifying a difference in electric potential between the reference electrode 3 and the detection electrode 6 as a bio-signal and supplies the amplified bio-signal to the filter 32. As explained earlier, the reference electrode 3 is provided on an end of the support plate 2 whereas the detection electrode 6 is connected to the support plate 2 through the connector 4 and the signal wire 5A.

The filter 32 has a band of frequencies of the measured bio-signal. To put it in detail, the filter 32 removes signal components each having a frequency outside the frequency band set for the filter 32 from the bio-signal and passes on the remaining signal components of the bio-signal to the A/D conversion block 33.

In this embodiment, the band of frequencies of the measured bio-signal is the band of frequencies of brain waves. A brain-wave signal is defined as a bio-signal from which signal components each having a frequency outside the frequency band of the brain waves have been removed. The filter 32 passes on the brain-wave signal to the A/D conversion block 33.

By the way, the brain waves having frequencies in the frequency band include a delta wave with frequencies in the range 1 to 3 Hz, a theta wave with frequencies in the range 4 to 7 Hz, an alpha wave with frequencies in the range 8 to 13 Hz, a beta wave with frequencies in the range 14 to 30 Hz, a gamma wave with frequencies in the range 31 to 64 Hz, an omega wave with frequencies in the range 65 to 128 Hz, a rho wave with frequencies in the range 129 to 512 Hz and a sigma wave with frequencies in the range 512 to 1,024 Hz. The frequency band covering some or all of these brain waves can be set by making use of the operation section.

The A/D conversion block 33 is a section for converting the analog brain-wave signal into digital data referred to hereafter as brain-wave data and supplying the brain-wave data to the analysis block 34.

The analysis block 34 is configured to employ a CPU (Central Processing Unit), a ROM (Read Only Memory) and a RAM (Random Access Memory) which serves as a work memory for the CPU. The ROM is a memory used for storing information including programs to be executed by the CPU to carry out analyses on the brain-wave data received from the A/D conversion block 33.

When the signal processing section 30 receives a command to start a measurement from the operation section, the analysis block 34 loads a program stored in the ROM into the RAM. The CPU then executes the program loaded in the RAM in order to carry out various kinds of processing and stores the brain-wave data received from the A/D conversion block 33 in the memory 35.

On the basis of the brain-wave data received from the A/D conversion block 33, the analysis block 34 determines whether the sleeping stage is a REM (Rapid Eye Movement) sleeping stage or a non-REM sleeping stage. Results of the stage determination are associated with the brain-wave data.

It is to be noted that the analysis block 34 determines whether the sleeping stage is a REM (Rapid Eye Movement) sleeping stage or a non-REM sleeping stage by making use of an appearance rate per unit time or a period of sustaining an appearance rate determined in advance as an element. Typical examples of the appearance rate per unit time are rates at which the delta wave, the theta wave and the alpha wave appear.

The communication block 36 is a section for transmitting brain-wave data received from the analysis block 34 or brain-wave data stored in the memory 35 to an external apparatus determined in advance by typically radio communications in accordance with a command received from the operation section.

1-3: Operations and Effects

In the configuration described above, the bio-signal measurement apparatus 1 employs a support plate 2 formed to fit the base of an auricle and a reference electrode 3 provided on one of the two ends of the support plate 2. In addition, the bio-signal measurement apparatus 1 also includes a main spring rod 5 and a detection electrode 6 connected to the support plate 2 through the main spring rod 5 which is a member made of a flexible material having a shape resembling a wire. The detection electrode 6 has a structure which can be held in an ear pocket.

When the bio-signal measurement apparatus 1 is installed on an auricle of a medical examinee, the bio-signal measurement apparatus 1 is brought into contact with the auricle and held firmly on the auricle because the reference electrode 3 is placed on the ear lobe whereas the detection electrode 6 is engaged with the ear pocket. With the bio-signal measurement apparatus 1 brought into contact with the auricle and held firmly on the auricle, a sufficient area of contact can be assured and the sensitivity of the measurement of bio-signals can be sustained at a certain level. Thus, the bio-signal measurement apparatus 1 is capable of acquiring waves propagating through the biological body of the medical examinee as a bio-signal directly without the need for the waves to propagate through an air layer.

In addition, the detection electrode 6 is engaged with the ear pocket facing a temporal bone and held firmly in the ear pocket. It is quite normal to assume a case in which the detection electrode 6 brought into contact with a pillow is further inserted by the pillow toward the inner side of the ear pocket typically when the medical examinee rolls over in bed during a sleep time. Even in such a case, the detection electrode 6 almost hardly hurt the medical examinee. Thus, the safety of the medical examinee can be assured better.

On top of that, in comparison with the known external auditory meatus electrode unit, the detection electrode 6 employed in the bio-signal measurement apparatus 1 does not choke up the external auditory meatus. Thus, the bio-signal measurement apparatus 1 is capable of providing the medical examinee with a comfortable apparatus-mounting feeling without raising a problem due to the fact that the medical examinee is forcibly put in a state where sounds are difficult to hear while the bio-signal measurement apparatus 1 is in a state of being installed on an auricle of the examinee.

In addition, the bio-signal measurement apparatus 1 is designed into such a configuration that, when the bio-signal measurement apparatus 1 is installed onto the auricle of an ear of a medical examinee, the aforementioned specific end of the detection electrode 6 employed in the bio-signal measurement apparatus 1 is engaged with the ear pocket. As described above, the ear pocket is the area between the crus of helix and the superior crux of antihelix of the auricle which is exposed to a temporal bone and contains almost no muscle. Thus, when the detection electrode 6 employed in the bio-signal measurement apparatus 1 is used for measuring brain waves, the measurement is almost not affected by a muscle electric potential. As a result, the brain waves can be measured with a high degree of precision.

In addition, as described above, the bio-signal measurement apparatus 1 is designed into such a configuration and the detection electrode 6 employed in the bio-signal measurement apparatus 1 is designed into such a shape that, when the bio-signal measurement apparatus 1 is installed on an auricle, the specific end of the detection electrode 6 is engaged with the ear pocket. Thus, when the detection electrode 6 is engaged with the ear pocket, the area of contact with the surface of the ear pocket can be increased. As a result, the sensitivity of the measurement of brain waves can be further improved.

On top of that, the bio-signal measurement apparatus 1 has a smaller area of contact with a pillow which is used during a sleep time. Thus, it is possible to considerably lower the level of disturbances experienced by the medical examinee during the sleep time.

In a configuration described above as the configuration of the bio-signal measurement apparatus 1, the reference electrode 3 is provided at a specific one of the two ends of the support plate 2 formed to fit the base of an auricle of an ear of a medical examinee. Thus, the bio-signal measurement apparatus 1 can come into contact with a surface exposed to bones surrounding the auricle while assuring the area of contact between the detection electrode 6 and the surface of the ear pocket. As a result, it is possible to raise the level of safety of the medical examinee while sustaining the sensitivity of the measurement of bio-signals at a certain level.

2: Second Embodiment 2-1: Configuration of the Bio-Signal Measurement Apparatus

Figure 6A:
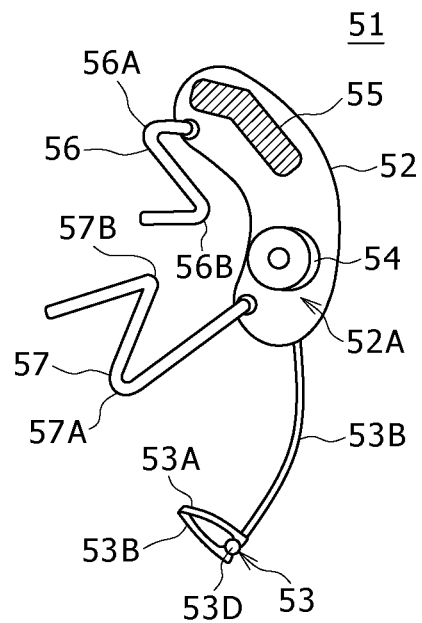
FIG. 6A is a top-view diagram roughly showing the bio-signal measurement apparatus according to a second embodiment.
Figure 6B:
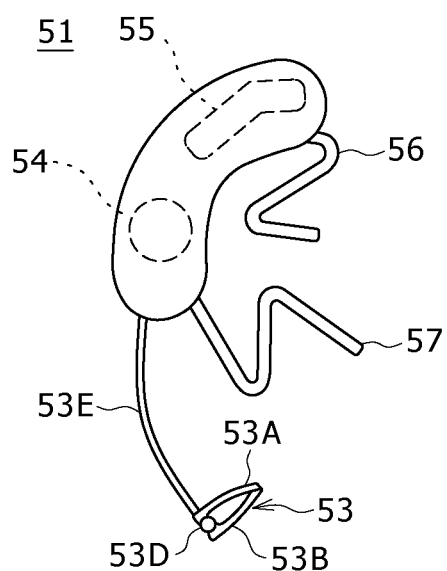
FIG. 6B is a bottom-view diagram roughly showing the bio-signal measurement apparatus according to the second embodiment.
Figure 6C:
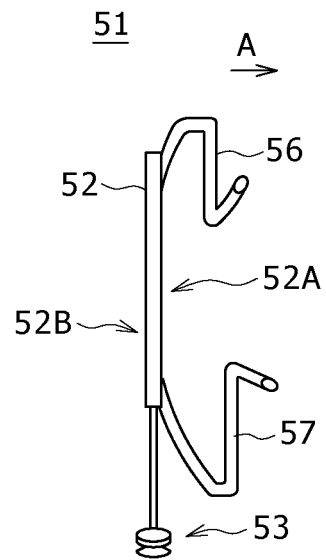
FIG. 6C is a side-view diagram roughly showing the bio-signal measurement apparatus according to the second embodiment.

As shown in the diagrams of FIGS. 6A, 6B and 6C, the bio-signal measurement apparatus 51 according to the second embodiment employs a support plate 52, a reference electrode 53, a first detection electrode 54, a second detection electrode 55, an upper-side hook 56 and a lower-side hook 57.

The support plate 52 is made from typically a plastic material. The support plate 52 is designed to have a shape resembling a bow that is formed to fit the base of the auricle of an ear. The support plate 52 is created to have such a length that, when the bio-signal measurement apparatus 51 is installed on an auricle, the support plate 52 is extended to fit the base of the auricle from a space between the upper-side portion of the base of an auricle and hair lines to a position exposed to a mastoid process.

The reference electrode 53 is connected by a signal wire 53E covered by a material such as vinyl to a specific one of the two ends of the support plate 52. The reference electrode 53 is a conductor made from typically a metallic material. The reference electrode 53 is configured to employ an electrode plate 53A, a clip 53B and a stud 53C as the reference electrode 3 employed in the bio-signal measurement apparatus 1 according to the first embodiment is configured to employ the electrode plate 3A, the clip 3B and the stud 3C.

The first detection electrode 54 is provided at a position on a contact surface 52A of the support plate 52. This position on the contact surface 52A is a position which is brought into contact with a surface exposed to the mastoid process of the medical examinee when the bio-signal measurement apparatus 51 is installed on the auricle. In the following description, the surface exposed to the mastoid process is referred to as a mastoid-process facing surface.

In addition, the second detection electrode 55 is also provided at another position on the contact surface 52A of the support plate 52. This other position on the contact surface 52A is a position which is brought into contact with another surface stretched from the space between the upper-side portion of the base of an auricle and hair lines to a location above the mastoid-process facing surface when the bio-signal measurement apparatus 51 is installed on the auricle. In the following description, this other surface stretched from the space between the upper-side portion of the base of an auricle and hair lines to the location above the mastoid-process facing surface is referred to as an above-ear surface.

On top of that, the upper-side hook 56 is also provided on the support plate 52. With the bio-signal measurement apparatus 51 installed on an auricle, a specific one of the two ends of the upper-side hook 56 is placed at a location in close proximity to the auricle. The upper-side hook 56 is a wire with the specific one of the two ends thereof covered by an elastic material such as rubber. The wire itself is made of a material such as metal.

The upper-side hook 56 is designed into a shape approximately resembling the letter Z which includes folding points 56A and 56B. The folding point 56A is a point at which the upper-side hook 56 is bent to fit the upper-side portion of the base of an auricle. The upper-side hook 56 is designed to include a portion created between the folding points 56A and 56B as a portion having such a length stretched in the longitudinal direction of the support plate 52 that, when the bio-signal measurement apparatus 51 is installed on an auricle, the folding point 56B is placed at a position between the triangular fossa and the concha.

In addition, the lower-side hook 57 is also provided on the support plate 52. With the bio-signal measurement apparatus 51 installed on an auricle, a specific one of the two ends of the lower-side hook 57 is placed at a location in close proximity to the auricle. The lower-side hook 57 is also a wire with the specific one of the two ends thereof covered by an elastic material such as rubber. The wire itself is made of a material such as metal.

The lower-side hook 57 is designed into a shape approximately resembling the letter Z which includes folding points 57A and 57B. The lower-side hook 57 is designed to include a portion created to start from the contact point between the lower-side hook 57 and the support plate 52 and end at the folding point 57A as a portion with such a length that, when the bio-signal measurement apparatus 51 is installed on an auricle, the folding point 57A is placed at a position below the ear lobe. The folding point 57A is a point at which the lower-side hook 57 is bent to fit the lower-side portion of the base of an auricle.

The lower-side hook 57 is designed to include also a portion created between the folding points 57A and 57B as a portion having such a length stretched in the longitudinal direction of the support plate 52 that, when the bio-signal measurement apparatus 51 is installed on an auricle, the folding point 57B is placed on the.

In addition, each of the upper-side hook 56 and the lower-side hook 57 is designed into a shape which is slightly bent in a direction departing from the rear face 52B of the support plate 52 to the contact surface 52A. In the side-view diagram of FIG. 6C, the direction departing from the rear face 52B of the support plate 52 is a direction indicated by an arrow A.

Inside the support plate 52, there is provided a signal processing section 60 which is not shown in the diagrams of FIGS. 6A, 6B and 6C. The signal processing section 60 is connected to the reference electrode 53, the first detection electrode 54 and the second detection electrode 55.

By the way, when the bio-signal measurement apparatus 51 is installed on the auricle of an ear of the medical examinee, first of all, the bio-signal measurement apparatus 51 is stretched to separate the upper-side hook 56 and the lower-side hook 57 from each other. Then, the support plate 52 is placed on the base of the auricle, the folding point 56A of the upper-side hook 56 is placed on the upper-side portion of the base whereas the folding point 57A of the lower-side hook 57 is placed at a position beneath the ear lobe.

Subsequently, the folding point 56B of the upper-side hook 56 is placed at a position between the triangular fossa and the concha whereas the folding point 57B of the lower-side hook 57 is brought into contact with the concha.

At that time, with the folding point 56B of the upper-side hook 56 serving as a support point, a force generated by the upper-side hook 56 to make an attempt to restore the upper-side hook 56 to the original shape of the upper-side hook 56 pulls the support plate 52, attaching the support plate 52 to the auricle. By the same token, with the folding point 57B of the upper-side hook 56 serving as a support point, a force generated by the lower-side hook 57 to make an attempt to restore the lower-side hook 57 to the original shape of the lower-side hook 57 pulls the support plate 52, attaching the support plate 52 to the auricle.

Figure 7A:
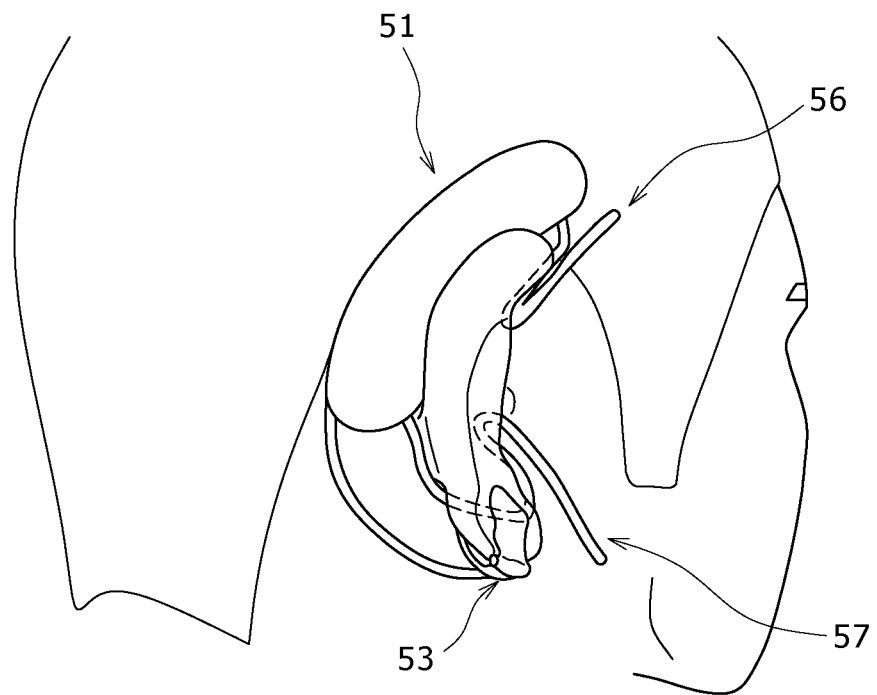
FIG. 7A is a diagram roughly showing a mounting state as seen from a position on a specific side of the apparatus.
Figure 7B:
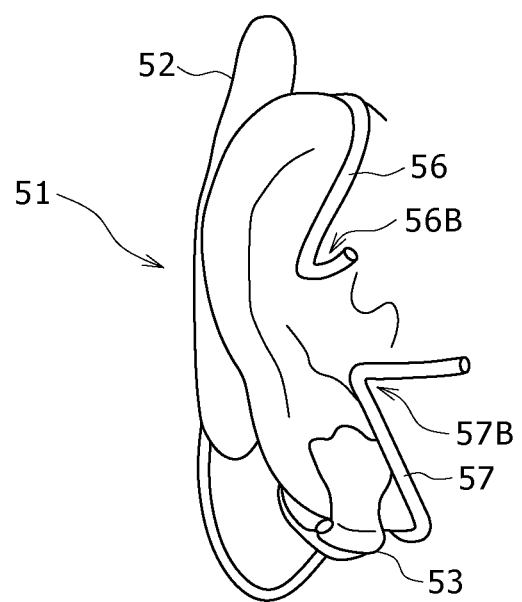
FIG. 7B is a diagram roughly showing a mounting state as seen from a position on a side other than the specific side of the apparatus.

As shown in the diagrams of FIGS. 7A and 7B, the upper-side hook 56 and the lower-side hook 57 thus pull the support plate 52, attaching the support plate 52 to the auricle. In this state, certain pulling forces firmly hold the support plate 52 on the auricle in such a way that the first detection electrode 54 and the second detection electrode 55 are brought into contact with the mastoid-process facing surface and the above-ear surface respectively.

In addition, the support plate 52 is firmly held on the auricle so that the ear lobe is sandwiched between the electrode plate 53A of the reference electrode 53 and the clip 53B of the reference electrode 53. In this state, the support plate 52 is firmly held on the auricle with the electrode plate 53A of the reference electrode 53 and the clip 53B of the reference electrode 53 brought into contact with the ear lobe. Thus, each of the electrode plate 53A of the reference electrode 53 and the clip 53B of the reference electrode 53 is capable of functioning as an electrode. It is to be noted that, since the electrode plate 53A of the reference electrode 53 has a shape resembling a coin with about the same size as the ear lobe, by sandwiching the ear lobe between the electrode plate 53A of the reference electrode 53 and the clip 53B of the reference electrode 53, the medical examinee is capable of carrying the bio-signal measurement apparatus 51 with ease.

As described above, when the bio-signal measurement apparatus 51 is installed on an auricle, the folding point 56B of the upper-side hook 56 is brought into contact with a portion between the triangular fossa and the concha whereas the folding point 57B of the lower-side hook 57 is brought into contact with the concha. In addition, the support plate 52 is brought into contact with the base of the auricle and firmly held on the auricle.

Since the forces for restoring each of the upper-side hook 56 and the lower-side hook 57 to the original shape press the support plate 52 against the auricle of an ear of the medical examinee and firmly hold the support plate 52 on the auricle, it is possible to prevent the bio-signal measurement apparatus 51 from falling off from the ear.

By deforming the upper-side hook 56 and the lower-side hook 57, the bio-signal measurement apparatus 51 can be installed on an auricle of the medical examinee or taken off from the auricle with ease. The upper-side hook 56 of the bio-signal measurement apparatus 51 is bent at the folding point 56A of the upper-side hook 56 whereas the lower-side hook 57 of the bio-signal measurement apparatus 51 is bent at the folding point 57A of the lower-side hook 57. Thus, in comparison with a configuration with upper-side and lower-side hook sections unbent, the bio-signal measurement apparatus 51 assures safety of the medical examinee and provides almost no pain to the examinee.

2-2: Configuration of the Signal Processing Section in the Support Plate

FIG. 8 is a circuit diagram showing the circuit configuration of a signal processing section 60 provided inside the support plate 52 51 according to the second embodiment. As shown in the figure, the signal processing section 60 employs a differential amplifier 61, a filter 62, an A/D conversion block 63, an analysis block 64, a memory 65 and a communication block 66.

In response to a measurement start command received from an operation section which is provided on the surface of the support plate 52, the signal processing section 60 supplies the voltage of a power supply such as a battery to the differential amplifier 61, the filter 62, the A/D conversion block 63, the analysis block 64, the memory 65 and the communication block 66. When a command to stop measurements of bio-signals is received from the operation section, on the other hand, the signal processing section 60 discontinues the operation to supply the voltage of a power supply such as a battery to the differential amplifier 61, the filter 62, the A/D conversion block 63, the analysis block 64, the memory 65 and the communication block 66.

The differential amplifier 61 is an amplifier for amplifying a difference in electric potential between the reference electrode 53 and the first detection electrode 54 as well as a difference in electric potential between the reference electrode 53 and the second detection electrode 55 as bio signals, supplying the amplified bio-signals to the filter 62.

The filter 62 is a section for setting a band of frequencies of bio-signals which each serve as a measurement subject. To put it in detail, the filter 62 removes signal components each having a frequency outside the frequency band set for the filter 62 from the bio-signal and passes on the remaining signal components of the bio-signal to the A/D conversion block 63.

The A/D conversion block 63 converts an analog brain-wave signal into digital brain-wave data and supplying the brain-wave data to the analysis block 64.

The analysis block 64 is configured to employ a CPU, a ROM and a RAM which serves as a work memory for the CPU. The ROM is a memory used for storing information including programs to be executed by the CPU to carry out analyses on the brain-wave data received from the A/D conversion block 63.

When the signal processing section 60 receives a command to start a measurement from the operation section mentioned above, the analysis block 64 loads a program stored in the ROM into the RAM. The CPU then executes the program loaded in the RAM in order to carry out various kinds of processing.

The analysis block 64 stores the brain-wave data received from the A/D conversion block 63 in the memory 65. In addition, on the basis of the brain-wave data received from the A/D conversion block 63, the analysis block 64 determines whether the sleeping stage is a REM (Rapid Eye Movement) sleeping stage or a non-REM sleeping stage. Results of the stage determination are associated with the brain-wave data.

The communication block 66 is a section for transmitting brain-wave data received from the analysis block 64 or brain-wave data stored in the memory 65 to an external apparatus determined in advance by typically radio communications in accordance with a command received from the operation section.

2-3: Measurement Results

Frequency analyses are carried out on brain-wave data detected at the first detection electrode 54 as results of measurements performed by the bio-signal measurement apparatus 51. The results of the measurements are shown in the diagram of FIG. 9A as a histogram representing relative magnitudes of alpha, delta theta and beta waves which are included in the brain-wave data.

In addition, for the aforementioned purpose of comparison with brain-wave data measured by the bio-signal measurement apparatus 51, a detection electrode is put on the head of the medical examinee whereas the reference electrode 53 employed in the bio-signal measurement apparatus 51 is used as a reference electrode, and brain-wave data is measured on the basis of a difference in electric potential between the reference electrode 53 and the detection electrode put on the head. The results of the measurements are shown in the diagram of FIG. 9B as a histogram representing relative magnitudes of alpha, delta theta and beta waves which are included in the brain-wave data.

As is obvious from the diagrams of FIGS. 9A and 9B, the first detection electrode 54 placed on the mastoid-process facing surface of the medical examinee results in almost the same relative magnitudes of detected brain-wave frequency components as those produced by the bio-signal measurement apparatus 51 with the detection electrode placed on the head of the examinee.

The histograms shown in the diagrams of FIGS. 9A and 9B indicate that, even in the case of the bio-signal measurement apparatus 51 having a configuration in which the reference electrode 53 is placed on the ear lobe of the medical examinee whereas the first detection electrode 54 is placed on the mastoid-process facing surface, it is possible to detect brain waves with almost the same degree of precision as a configuration including a detection electrode placed on the head of the examinee.

It is to be noted that, by making use of the second detection electrode 55 placed on the above-ear surface of the medical examinee, the bio-signal measurement apparatus 51 is also capable of detecting brain waves with almost the same degree of precision as the configuration which includes a detection electrode placed on the head of the examinee.

2-4: Operations and Effects

In the configuration described above as the configuration of the bio-signal measurement apparatus 51, the contact surface 52A has a shape which is formed to fit the base of the auricle. The contact surface 52A is exposed to the surface of a space between the upper-side portion of the base of an auricle and hair lines when the bio-signal measurement apparatus 51 is installed on the auricle.

In addition, the bio-signal measurement apparatus 51 is also provided with the reference electrode 53 which is connected to a specific one of the two ends of the support plate 52 through the signal wire 53E. On top of that, the bio-signal measurement apparatus 51 is also provided with the first detection electrode 54 on a portion which exists on the contact surface 52A of the support plate 52 as a portion exposed to a mastoid process. In addition, the bio-signal measurement apparatus 51 is also provided with the second detection electrode 55 on a portion which exists on the contact surface 52A of the support plate 52 as a portion exposed to the surface of a space between the upper-side portion of the base of an auricle and hair lines.

When the bio-signal measurement apparatus 51 is installed on an auricle of the medical examinee, the reference electrode 53 employed in the bio-signal measurement apparatus 51 is placed on the ear lobe, the first detection electrode 54 employed in the bio-signal measurement apparatus 51 is brought into contact with the mastoid-process facing surface whereas the second detection electrode 55 employed in the bio-signal measurement apparatus 51 is brought into contact with the above-ear surface. It is thus possible to assure a sufficient contact surface and sustain the sensitivity of the measurement of bio-signals at a certain level. As a result, the bio-signal measurement apparatus 51 is capable of acquiring waves propagating through the biological body of the examinee as a bio-signal directly without the need for the waves to propagate through an air layer.

In addition, when the bio-signal measurement apparatus 51 is installed on an auricle of the medical examinee, the first detection electrode 54 and the second detection electrode 55 are brought into contact with a surface which is exposed to a temporal bone. Thus, even for a case in which the first detection electrode 54 and the second detection electrode 55 are brought into contact with a pillow typically when the medical examinee rolls over in bed during a sleep time, the bio-signal measurement apparatus 51 is capable of assuring safety of the medical examinee and providing almost no pain to the examinee.

In comparison with the known external auditory meatus electrode unit, the first detection electrode 54 and the second detection electrode 55 which are employed in the bio-signal measurement apparatus 51 do not choke up the external auditory meatus. Thus, the bio-signal measurement apparatus 51 is capable of providing the medical examinee with a comfortable apparatus-mounting feeling without raising a problem that the medical examinee is forcibly put in a state where sounds are difficult to hear while the bio-signal measurement apparatus 51 is in a state of being installed on an auricle of the examinee.

The bio-signal measurement apparatus 51 is designed into such a configuration that, when the bio-signal measurement apparatus 51 is installed onto the auricle of an ear of a medical examinee, the aforementioned specific ends of the first and second detection electrodes 54 and 55 employed in the bio-signal measurement apparatus 51 are placed on respectively the mastoid-process facing surface and the above-ear surface which are exposed to a temporal bone and contains almost no muscle. Thus, when the first and second detection electrodes 54 and 55 employed in the bio-signal measurement apparatus 51 are used for measuring brain waves, the measurement is almost not affected by a muscle electric potential. As a result, the brain waves can be measured with a high degree of precision.

On top of that, the bio-signal measurement apparatus 51 has a smaller area of contact with a pillow which is used during a sleep time. Thus, it is possible to considerably lower the level of disturbances experienced by the medical examinee during the sleep time.

In addition, the bio-signal measurement apparatus 51 is provided with the upper-side hook 56 having the folding point 56B which is brought into contact with a portion between the triangular fossa and the concha. The upper-side hook 56 has a shape which is bent at the folding point 56A to fit the upper-side portion of the base of the auricle. The upper-side hook 56 is a member which has a shape resembling a wire. The upper-side hook 56 is connected to the upper-side portion of the support plate 52.

On top of that, the bio-signal measurement apparatus 51 is also provided with the lower-side hook 57 having the folding point 57B which is brought into contact with the concha. The lower-side hook 57 is bent at the folding point 57A to fit the lower-side portion of the base of the auricle. The lower-side hook 57 is also a member which has a shape resembling a wire. The lower-side hook 57 is connected to the lower-side portion of the support plate 52.

With the configuration described above, when the bio-signal measurement apparatus 51 is installed on an auricle of the medical examinee, the support plate 52 is pressed against the auricle of the medical examinee the folding point 56B and the folding point 57B as support points. Thus, it is possible to prevent the bio-signal measurement apparatus 51 from falling off from the ear.

In accordance with the configuration described above, the bio-signal measurement apparatus 51 employs the support plate 52 which is formed to fit the base of the auricle and has the contact surface 52A exposed to a surface between the base of the auricle and hair lines. On top of that, the bio-signal measurement apparatus 51 also employs the reference electrode 53 which is brought into contact with the ear lobe. In addition, the bio-signal measurement apparatus 51 also employs the first detection electrode 54 and the second detection electrode 55 which are provided on the contact surface 52A. Thus, the bio-signal measurement apparatus 51 comes into contact with a surface exposed to a temporal bone while assuring the area of contact between the first detection electrode 54 and the mastoid-process facing surface as well as the area of contact between the second detection electrode 55 and the above-ear surface. As a result, it is possible to raise the level of safety of the medical examinee while sustaining the sensitivity of the measurement of bio-signals at a certain level.

3: Third Embodiment 3-1: Configuration of the Bio-Signal Measurement Apparatus

Figure 10:
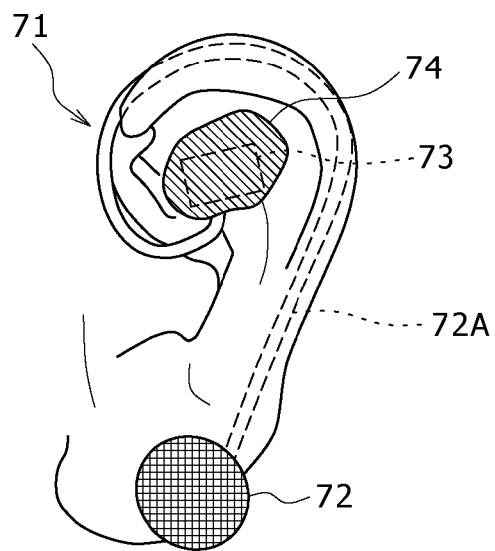
FIG. 10 is a diagram roughly showing a bio-signal measurement apparatus according to a third embodiment.

FIG. 10 is a diagram roughly showing a bio-signal measurement apparatus 71 according to a third embodiment. As shown in the figure, the bio-signal measurement apparatus 71 according to the third embodiment employs a reference electrode 72, a detection electrode 73 and an electrode pressing section 74 for pressing the detection electrode 73 against the ear pocket.

The reference electrode 72 is a conductor which is made from typically a metallic material. The reference electrode 72 employs an electrode plate, a clip and a link section having configurations identical with those of respectively the electrode plate 3A, the clip 3B and the stud 3C which are employed in the reference electrode 3 of the bio-signal measurement apparatus 1 according to the first embodiment explained earlier.

The detection electrode 73 is also a conductor which has a shape resembling a plate. The detection electrode 73 is brought into contact with the ear pocket to fit the crus of helix and the inferior crux of antihelix. The electrode pressing section 74 placed above the detection electrode 73 presses down the detection electrode 73 in the downward direction.

The electrode pressing section 74 is a section which is made from typically a clay material. The detection electrode 73 is sandwiched between the electrode pressing section 74 and the surface of the ear pocket. The electrode pressing section 74 has a flexible shape which fits the ear pocket so that the detection electrode 73 is brought into contact with the ear pocket.

A signal processing section 80 not shown in the diagram of FIG. 10 is provided inside the electrode pressing section 74. The signal processing section 80 is connected to the detection electrode 73. In addition, the signal processing section 80 is also connected to the reference electrode 72 through a signal wire 72A.

3-2: Configuration of the Signal Processing Apparatus

Figure 11:
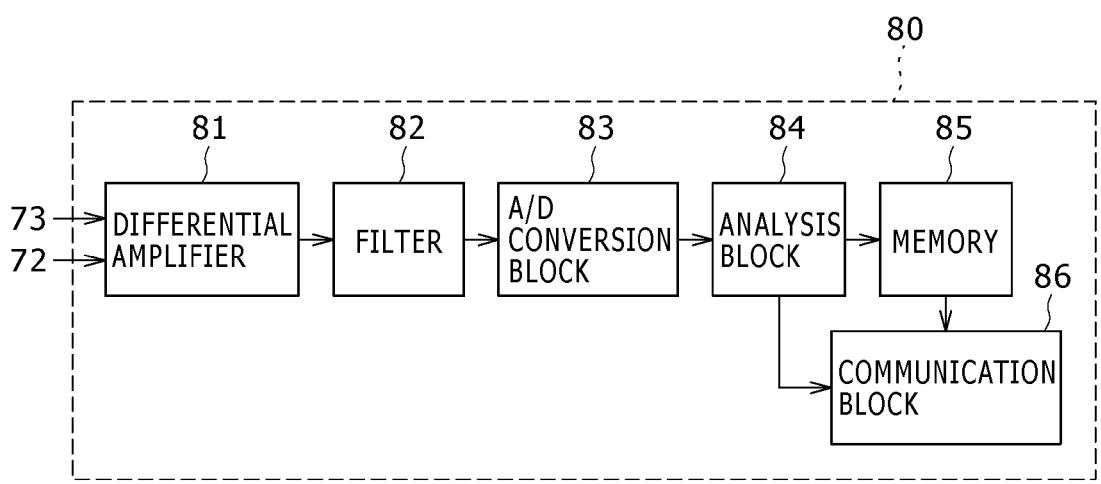
FIG. 11 is a circuit diagram showing the circuit configuration of a signal processing section employed in the bio-signal measurement apparatus according to the third embodiment.

FIG. 11 is a circuit diagram showing the circuit configuration of the signal processing section 80 employed in the bio-signal measurement apparatus 71 according to the third embodiment. As described above, the signal processing section 80 is provided inside the electrode pressing section 74. As shown in the figure, the signal processing section 80 is configured to employ a differential amplifier 81, a filter 82, an A/D (Analog-to-Digital) conversion section 83, an analysis block 84, a memory 85 and a communication block 86.

The differential amplifier 81 is an amplifier for amplifying a difference in electric potential between the reference electrode 72 and the detection electrode 73 as a bio-signal, supplying the amplified bio-signal to the filter 82.

The filter 82 is a section for setting a band of frequencies of bio-signals which each serve as a measurement subject. To put it in detail, the filter 82 removes signal components each having a frequency outside the frequency band set for the filter 82 from the bio-signal and passes on the remaining signal components of the bio-signal to the A/D conversion block 83.

The A/D conversion block 83 is a section for converting an analog brain-wave signal, which is the bio-signal passed on by the filter 82 to the A/D conversion block 83, into digital brain-wave data and supplying the brain-wave data to the analysis block 84.

The analysis block 84 is configured to employ a CPU, a ROM and a RAM which serves as a work memory for the CPU. The ROM is a memory used for storing information including programs to be executed by the CPU to carry out analyses on the brain-wave data received from the A/D conversion block 83.

When the signal processing section 80 receives a command to start a measurement from an operation section, the analysis block 84 loads a program stored in the ROM into the RAM. The CPU then executes the program loaded in the RAM in order to carry out various kinds of processing.

The analysis block 84 stores the brain-wave data received from the A/D conversion block 83 in the memory 85. In addition, on the basis of the brain-wave data received from the A/D conversion block 83, the analysis block 84 determines whether the sleeping stage is a REM sleeping stage or a non-REM sleeping stage. Results of the stage determination are associated with the brain-wave data.

The communication block 86 is a section for transmitting brain-wave data received from the analysis block 84 or brain-wave data stored in the memory 85 to an external apparatus determined in advance by typically radio communications in accordance with a command received from the operation section.

3-3: Measurement Results

Frequency analyses are carried out on brain-wave data detected at the detection electrode 73 as results of measurements performed by the bio-signal measurement apparatus 71. The results of the measurements are show in the diagram of FIG. 12A as a histogram representing relative magnitudes of alpha, delta, theta and beta waves which are included in the brain-wave data.

In addition, for the aforementioned purpose of comparison with brain-wave data measured by the bio-signal measurement apparatus 71, a detection electrode is put on the head of the medical examinee whereas the reference electrode 72 employed in the bio-signal measurement apparatus 71 is used as a reference electrode, and brain-wave data is measured on the basis of a difference in electric potential between the reference electrode 72 and the detection electrode put on the head. The results of the measurements are show in the diagram of FIG. 12B as a histogram representing relative magnitudes of alpha, delta, theta and beta waves which are included in the brain-wave data.

Figure 12A:
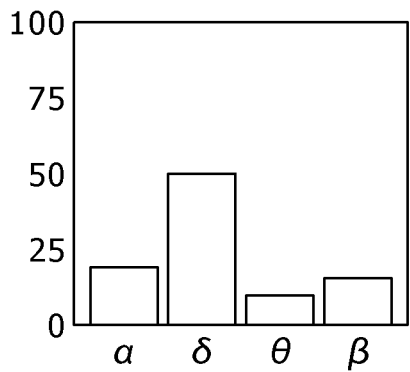
FIG. 12A is a diagram showing typical results of the brain-wave measurements according to the third embodiment.
Figure 12B:
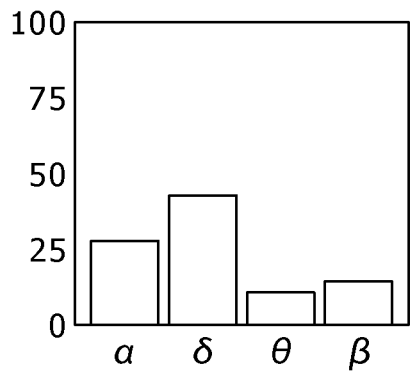
FIG. 12B is a diagram showing other typical results of the brain-wave measurements according to the third embodiment.

As is obvious from the diagrams of FIGS. 12A and 12B, the detection electrode 73 placed in the ear pocket of the medical examinee results in almost the same relative magnitudes of detected brain-wave frequency components as those produced by the bio-signal measurement apparatus 71 with the detection electrode placed on the head of the examinee.

The histograms shown in the diagrams of FIGS. 12A and 12B indicate that, even in the case of the bio-signal measurement apparatus 71 having a configuration in which the reference electrode 72 is placed on the ear lobe of the medical examinee whereas the detection electrode 73 is placed in the ear pocket, it is possible to detect brain waves with almost the same degree of precision as a configuration including a detection electrode placed on the head of the examinee.

3-4: Operations and Effects

In accordance with the configuration described above, the bio-signal measurement apparatus 71 employs the reference electrode 72 to be placed on the ear lobe of the medical examinee, the detection electrode 73 to be brought into contact with the surface of the ear pocket and the electrode pressing section 74 for supporting the reference electrode 72 through the signal wire 72A as well as supporting the detection electrode 73.

When the bio-signal measurement apparatus 71 is installed on an auricle of the medical examinee, the reference electrode 72 is placed on the ear lobe of the medical examinee whereas the electrode pressing section 74 made from typically a clay material is deformed into the shape of the ear pocket so as to sandwich the detection electrode 73 between the electrode pressing section 74 and the surface of the ear pocket.

Thus, the detection electrode 73 is capable of assuring a sufficient area of contact with the ear pocket and sustaining the sensitivity of the measurement of bio-signals at a certain level. As a result, the bio-signal measurement apparatus 71 is capable of acquiring waves propagating through the biological body of the examinee as a bio-signal directly without the need for the waves to propagate through an air layer.

In addition, the detection electrode 73 employed in the bio-signal measurement apparatus 71 is brought into contact with the ear pocket which is exposed to a temporal bone. Thus, even for a case in which the detection electrode 73 is brought into contact with a pillow typically when the medical examinee rolls over in bed during a sleep time, the bio-signal measurement apparatus 71 is capable of assuring safety of the medical examinee and providing almost no pain to the examinee.

In comparison with the external auditory meatus electrode unit hitherto known, the detection electrode 73 employed in the bio-signal measurement apparatus 71 does not choke up the external auditory meatus. Thus, the bio-signal measurement apparatus 71 is capable of providing the medical examinee with a comfortable apparatus-mounting feeling without raising a problem that the medical examinee is forcibly put in a state where sounds are difficult to hear while the bio-signal measurement apparatus 71 is in a state of being installed on an auricle of the examinee.

On top of that, the bio-signal measurement apparatus 71 has a smaller area of contact with a pillow which is used during a sleep time. Thus, it is possible to considerably lower the level of disturbances experienced by the medical examinee during the sleep time.

In accordance with the configuration described above, the bio-signal measurement apparatus 71 employs the reference electrode 72 to be placed on the ear lobe of the medical examinee, the detection electrode 73 to be brought into contact with the surface of the ear pocket and the electrode pressing section 74 for supporting the reference electrode 72 through the signal wire 72A as well as supporting the detection electrode 73. Thus, with the bio-signal measurement apparatus 71 brought into contact with a surface exposed to a temporal bone, the bio-signal measurement apparatus 71 is capable of assuring a sufficient area of contact between the detection electrode 73 and the ear pocket. As a result, the bio-signal measurement apparatus 71 is capable of better assuring the safety of the medical examinee and sustaining the sensitivity of the measurement of bio-signals at a certain level.

4: Other Embodiments

The first embodiment described before implements the bio-signal measurement apparatus 1 including the signal processing section 30 provided in the support plate 2. By the same token, the second embodiment described earlier implements the bio-signal measurement apparatus 51 including the signal processing section 60 provided in the support plate 52 whereas the third embodiment also explained before implements the bio-signal measurement apparatus 71 including the signal processing section 80 provided in the electrode pressing section 74. It is to be noted, however, that the scope is by no means limited to the first, second and third embodiments. For example, it is possible to provide an embodiment implementing a bio-signal measurement apparatus in which the signal processing section 30 is provided separately from the support plate 2 and connected to each of the reference electrode 3 and the detection electrode 6 by making use of a cable determined in advance. As another example, the signal processing section 60 of the second embodiment can be physically separated from the support plate 52. As a further example, the signal processing section 80 of the third embodiment can be physically separated from the electrode pressing section 74.

In addition, in the case of the first, second and third embodiments, the analysis blocks 34, 64 and 84 store brain-wave data in the memories 35, 65 and 85 respectively in accordance with a command to start a measurement of brain waves upon receiving the command. It is to be noted, however, that the scope is by no means limited to the first, second and third embodiments. For example, in the case of the first, second and third embodiments, an average levels of brain-wave data received from the A/D conversion blocks 33, 63 and 83 respectively during a predetermined period beginning from a measurement start point is compared with a non-contact level threshold value. In the following description, the predetermined period beginning from a measurement start point is referred to as a calibration period.

In the case of the first, second and third embodiments, if the average of brain-wave data levels obtained during the calibration period is found smaller than the non-contact level threshold value, the analysis blocks 34, 64 and 84 regard the brain-wave data level average smaller than the non-contact level threshold value as an indicator which shows that the detection electrode 6 is in a non-contact state. In this case, the analysis blocks, 34, 64 and 84 may issue a message, which states that the bio-signal measurement apparatus 1, 51 and 71 should be reinstalled on the auricle, to a speaker (not shown) provided on typically the support plates 2 and 52.

In addition, in the case of the first embodiment, the detection electrode 6 is a conductor, a specific one of the two ends of which has a shape approximately resembling a round cone. The bio-signal measurement apparatus 1 is created into such a configuration that, when the bio-signal measurement apparatus 1 is installed onto the auricle of an ear of a medical examinee, the aforementioned specific end of the detection electrode 6 employed in the bio-signal measurement apparatus 1 is engaged with the ear pocket. In addition, the detection electrode 6 is designed into such a shape that, when the specific end of the detection electrode 6 is engaged with the ear pocket or when the specific end of the detection electrode 6 has been put in a state of being engaged with the ear pocket, the conical surface of the specific end of the detection electrode 6 is brought into contact with the surface of the ear pocket. It is to be noted, however, that the scope is by no means limited to the first embodiment and the form of the detection electrode 6 is by no means limited to a form, a specific one of the two ends of which has a shape approximately resembling a round cone. For example, it is possible to provide another embodiment which is described as follows.

Figure 13A:
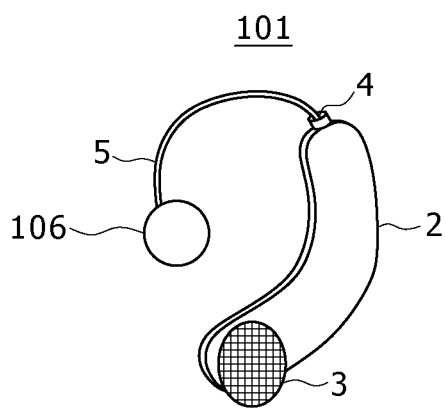
FIG. 13A is a diagram roughly showing an implementation of the bio-signal measurement apparatus according to the first other embodiment.
Figure 13B:
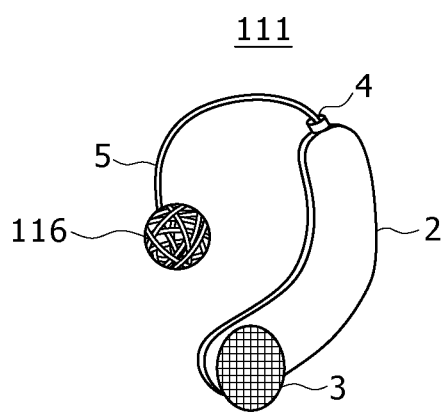
FIG. 13B is a diagram roughly showing another implementation of the bio-signal measurement apparatus according to the first other embodiment.

In FIGS. 13A and 13B, components identical with their respective counterparts employed in the bio-signal measurement apparatus 1 shown in the diagram of FIGS. 1A and 1B are denoted by the same reference numerals as the counterparts. As shown in the diagram of FIG. 13A, the bio-signal measurement apparatus 101 employs a detection electrode 106 in place of the detection electrode 6 employed in the bio-signal measurement apparatus 1. The detection electrode 106 is a conductor having a spherical shape, the size of which is a little larger than that of the ear pocket.

When the bio-signal measurement apparatus 101 is installed on an auricle of the medical examinee, the detection electrode 106 is inserted into the ear pocket to be engaged with the ear pocket by widening the ear pocket. This is because the detection electrode 106 has a spherical shape, the size of which is a little larger than that of the ear pocket.

Thus, a force making an attempt to restore members surrounding the ear pocket to their original positions is applied to the detection electrode 106. This force firmly holds the detection electrode 106 in the ear pocket, preventing the detection electrode 106 from moving along the inside of the ear pocket. In addition, the force closely attaches the detection electrode 106 to the surface of the ear pocket, hence, increasing the area of contact between the detection electrode 106 and the surface of the ear pocket. As a result, the sensitivity of detection of a bio-signal is increased.

It is to be noted that the shape of the detection electrode 106 is by no means limited to the spherical shape. That is to say, the detection electrode 106 can have another shape such as a half-spherical shape or a conical shape as long as the other shape causes a force of restoring members surrounding the ear pocket to their original positions to be applied to the detection electrode 106 and to firmly hold the detection electrode 106 in the ear pocket when the detection electrode 106 is inserted into the ear pocket to be engaged with the ear pocket by widening the ear pocket.

On the other hand, the bio-signal measurement apparatus 111 shown in the diagram of FIG. 13B as another implementation of the first other embodiment employs a detection electrode 116 in place of the detection electrode 6 employed in the bio-signal measurement apparatus 1. The detection electrode 116 is a conductor having a net-like structure which exhibits a slightly strong elastic property with respect to the ear pocket. As described above, in the diagram of FIG. 13B, components identical with their respective counterparts employed in the bio-signal measurement apparatus 1 shown in the diagram of FIGS. 1A and 1B are denoted by the same reference numerals as the counterparts.

To put it in detail, the detection electrode 116 is made by plain-weaving a conductive metallic plate in such a way that the conductive metallic plate is formed into approximately a circular shape which has a size a little larger than that of the ear pocket.

When the bio-signal measurement apparatus 111 is installed on an auricle of the medical examinee, the detection electrode 116 is inserted into the ear pocket to be engaged with the ear pocket in a state of being screwed. This is because the detection electrode 116 has a spherical shape, the size of which is a little larger than that of the ear pocket, and exhibits a slightly strong elastic property with respect to the ear pocket.

Thus, a force making an attempt to restore members surrounding the ear pocket to their original positions is applied to the detection electrode 116. This force firmly holds the detection electrode 116 in the ear pocket, preventing the detection electrode 116 from moving along the inside of the ear pocket. In addition, the force closely attaches the detection electrode 116 to the surface of the ear pocket, hence, increasing the area of contact between the detection electrode 116 and the surface of the ear pocket. As a result, the sensitivity of detection of a bio-signal is increased.

It is to be noted that the detection electrode 116 can also be created by rounding a conductor having a wire-like shape or a plate-like shape provided that the resulting detection electrode 116 exhibits a slightly strong elastic property with respect to the ear pocket. It is desirable to create the detection electrode 116 by making use of a conductor having a fine wire-like shape or a fine plate-like shape so that a larger area of contact between the detection electrode 116 and the surface of the ear pocket is formed when the bio-signal measurement apparatus 111 is installed on an auricle of the medical examinee.

In the case of the first embodiment described before, the detection unit 7 includes the connector 4, the main spring rod 5 and the detection electrode 6. It is to be noted, however, that implementations are by no means limited to such a configuration. For example, the length and shape of the main spring rod 5 can be changed to create a variety of detection units 7 to be used in conjunction with the support plate 2.

By providing the main spring rod 5 employed in the bio-signal measurement apparatus 1 according to the first embodiment described earlier with a changeable elastic form, even if there are individual differences in auricle shape among medical examinees to a certain degree, the detection electrode 6 can be engaged with the ear pocket or the external auditory meatus. If the individual difference is big as is the case with the difference in auricle shape between an adult and a child, however, the individual difference cannot be absorbed in some cases.

In such cases, by selecting a detection unit 7 fitting the shape of an auricle of the medical examinee from the various detection units, the bio-signal measurement apparatus 1 can be installed on the auricle of the medical examinee and the medical examinee can be provided with a comfortable apparatus-mounting feeling. A detection unit 7 fitting the shape of an auricle of the medical examinee is a detection unit 7 employing a main spring rod 5 having a length and a shape which are proper for the auricle.

In addition, the first embodiment described earlier employs one detection unit 7, which has the connector 4, the main spring rod 5 and the detection electrode 6, for the support plate 2. It is to be noted, however, that implementations are by no means limited to the first embodiment. That is to say, for the support plate 2, a plurality of detection units 7 can be provided.

Figure 14:
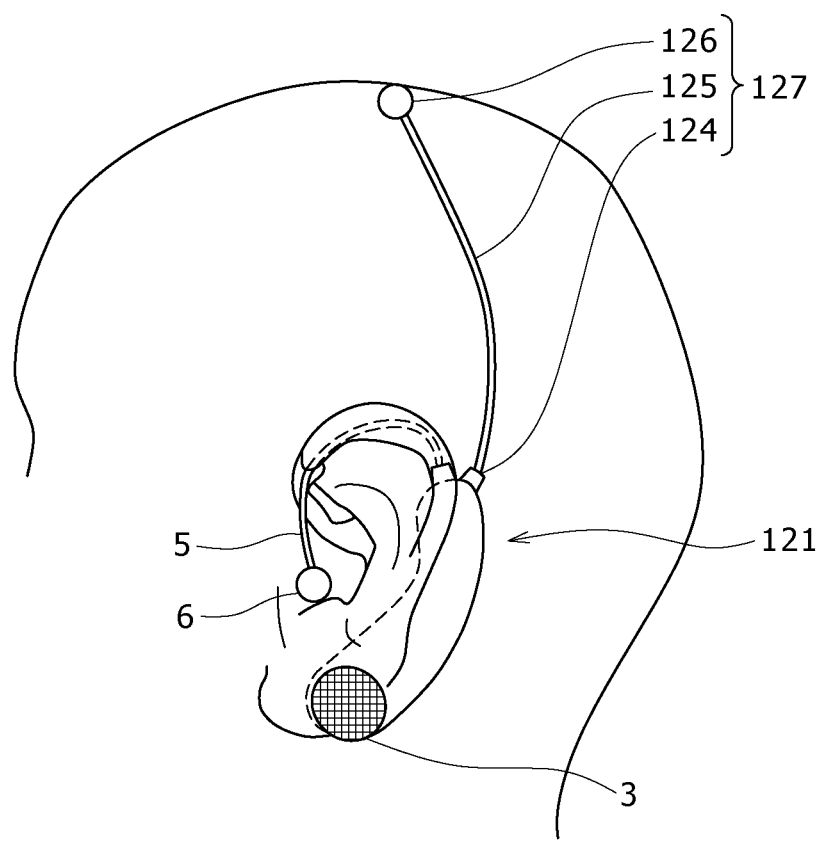
FIG. 14 is a diagram roughly showing a bio-signal measurement apparatus according to a second other embodiment.

FIG. 14 is a diagram roughly showing a bio-signal measurement apparatus 121 according to a second other embodiment which serves as another typical example of the other embodiments. In the diagram of FIG. 14, components identical with their respective counterparts employed in the bio-signal measurement apparatus 1 shown in the diagram of FIGS. 1A and 1B are denoted by the same reference numerals as the counterparts. As shown in the figure, in addition to the detection unit 7, the bio-signal measurement apparatus 121 also employs a detection unit 127 which has a connector 124, a main spring rod 125 and a detection electrode 126.

In the same way as the bio-signal measurement apparatus 1, when the bio-signal measurement apparatus 121 is installed on an auricle of the medical examinee, the bio-signal measurement apparatus 121 is firmly held on the auricle of the medical examinee by the reference electrode 3, the main spring rod 125 and the detection electrode 126.

In addition, in the case of the bio-signal measurement apparatus 121, the main spring rod 125 is stretched so as to separate the detection electrode 126 away from the support plate 2. With the main spring rod 125 stretched, the detection electrode 126 can be placed at a left center C3 which is determined in accordance with the international 10-20 system of electrode placement. A force making an attempt to restore the main spring rod 125 to its original shape presses the detection electrode 126 against the head skin, firmly holding the detection electrode 126 on the head skin.

When the signal processing section 30 receives a command from the operation section as a command to start a measurement of bio-signals, the signal processing section 30 amplifies a difference in electric potential between the reference electrode 3 and the detection electrode 126 and stores brain-wave data with frequencies included in a set range of frequencies of bio-signals each serving as a measurement subject into the memory 35 employed in the signal processing section 30.

By providing the bio-signal measurement apparatus 121 with an additional simple configuration including the detection unit 127 as described above, the bio-signal measurement apparatus 121 becomes capable of detecting brain waves observed at a measurement position which is closer to the brain.

It is to be noted that the detection electrode 126 can be placed on the head of the medical examinee at any other arbitrary position determined in accordance with the international 10-20 system of electrode placement to serve as a position different from the left center C3 cited earlier. Typical examples of the other position are a left frontal pole Fp1, a right frontal pole Fp2, a left frontal F3, a right frontal F4, a right center C4, a left parietal P3 and a right parietal P4.

Figure 15:
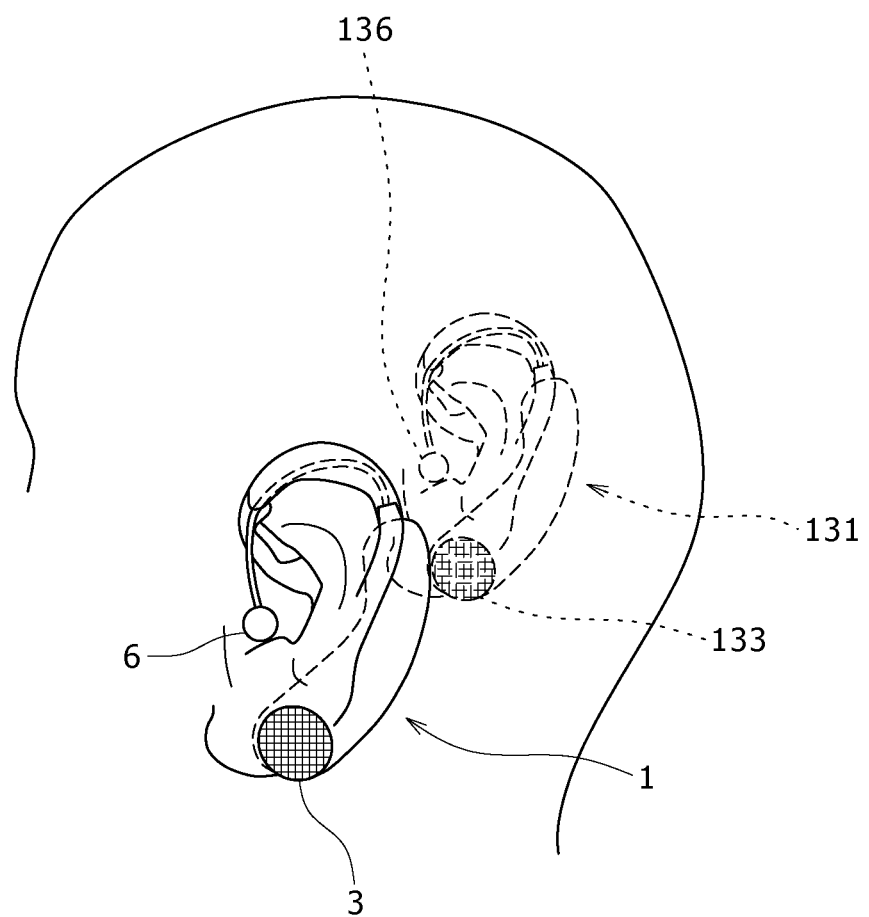
FIG. 15 is a diagram roughly showing the bio-signal measurement apparatus according to the first embodiment and a bio-signal measurement apparatus according to a third other embodiment.

In addition, the bio-signal measurement apparatus 1 according to the first embodiment, the bio-signal measurement apparatus 51 according to the second embodiment or the bio-signal measurement apparatus 71 according to the third embodiment is installed on one of the auricles of the medical examinee in order to measure brain waves. It is to be noted, however, that implementations are by no means limited to the first, second and third embodiments. As a further example, FIG. 15 roughly shows the bio-signal measurement apparatus 1 according to the first embodiment and a bio-signal measurement apparatus 131 according to a third other embodiment. In the diagram of FIG. 15, components identical with their respective counterparts employed in the bio-signal measurement apparatus 1 shown in the diagram of FIGS. 1A and 1B are denoted by the same reference numerals as the counterparts. As shown in the diagram of FIG. 15, the bio-signal measurement apparatus 1 and 131 are installed on respectively the 2 auricles of the medical examinee in order to measure brain waves.

In the case of this configuration, a signal processing section employed in at least one of the bio-signal measurement apparatus 1 and 131 receives signals generated by the reference electrode 3 and the detection electrode 6 which are included in the bio-signal measurement apparatus 1 as well as bio-signals generated by the reference electrode 133 and the detection electrode 136 which are included in the bio-signal measurement apparatus 131. It is to be noted that the signal processing section itself is not shown in the diagram of FIG. 15.

The signal processing section detects a difference in electric potential between the reference electrode 3 employed in the bio-signal measurement apparatus 1 and the detection electrode 136 employed in the bio-signal measurement apparatus 131 as a brain-wave signal, or detects a difference in electric potential between the detection electrode 6 employed in the bio-signal measurement apparatus 1 and the reference electrode 133 employed in the bio-signal measurement apparatus 131 as a brain-wave signal.

To put it in detail, the signal processing section employed in the bio-signal measurement apparatus 1 installed on specific one of the auricles of the medical examinee detects a difference in electric potential between the reference electrode 3 employed in the bio-signal measurement apparatus 1 and the detection electrode 136 employed in the bio-signal measurement apparatus 131, which is installed on the other one of the 2 auricles, as a brain-wave signal. On the other hand, the signal processing section employed in the bio-signal measurement apparatus 131 installed on the other auricle detects a difference in electric potential between the reference electrode 133 employed in the bio-signal measurement apparatus 131 and the detection electrode 6 employed in the bio-signal measurement apparatus 1, which is installed on the specific auricle, as a brain-wave signal. Thus, since the distance between the reference electrode 3 employed in the bio-signal measurement apparatus 1 installed on the specific auricle and the detection electrode 136 employed in the bio-signal measurement apparatus 131 installed on the other auricle is relatively long in comparison with the distance between the reference and detection electrodes 3 and 6 employed in the bio-signal measurement apparatus 1 as well as the distance between the reference and detection electrodes 133 and 136 employed in the bio-signal measurement apparatus 131, the level of the detected brain-wave signal is relatively high so that the detection precision is also relatively high as well. By the same token, since the distance between the reference electrode 133 employed in the bio-signal measurement apparatus 131 installed on the other auricle and the detection electrode 6 employed in the bio-signal measurement apparatus 1 installed on the specific auricle is relatively long in comparison with the distance between the reference and detection electrodes 3 and 6 employed in the bio-signal measurement apparatus 1 as well as the distance between the reference and detection electrodes 133 and 136 employed in the bio-signal measurement apparatus 131, the level of the detected brain-wave signal is relatively high so that the detection precision is also relatively high as well.

In addition, the second embodiment explained before includes two detection electrodes, i. e., the first detection electrode 54 and the second detection electrode 55. It is to be noted, however, that implementations are by no means limited to the second embodiment. That is to say, it is possible to provide an embodiment which includes only either one of the first detection electrode 54 and the second detection electrode 55.

On top of that, in the first, second and third embodiments explained before, the subject of measurements is brain waves. However, the subject of measurements can also be muscle electric potentials. As a matter of fact, it is also possible to provide a bio-signal measurement apparatus in which the subject of measurements can be switched from brain waves to muscle electric potentials and vice versa. It is to be noted that, in the case of a bio-signal measurement apparatus in which muscle electric potentials are taken as the subject of measurements, a band of frequencies of bio-signals each representing a muscle electric potential is set for the filter 32, 62 or 82. That is to say, the filter 32, 62 or 82 removes signal components each having a frequency outside the frequency band from a bio-signal.

In the case of the second embodiment explained before, a radiation temperature sensor can be provided on the folding point 57B of the lower-side hook 57. As described before, the lower-side hook 57 has a shape bent a little and the folding point 57B is positioned to surround the external auditory meatus. Thus, by providing a radiation temperature sensor on the folding point 57B, it is possible to measure the temperature of the innermost portion of the external auditory meatus.

In addition, in each of the first, second and third embodiments explained before, the detection electrode can be placed on the head, an eye socket or a chin and a cable determined in advance is used for connecting the detection electrode to the signal processing section employed in the bio-signal measurement apparatus 1, the bio-signal measurement apparatus 51 or the bio-signal measurement apparatus 71 respectively. In the case of such a bio-signal measurement apparatus, the cable determined in advance can be conceivably designed by properly applying the configuration of the main spring rod 5 employed in the first embodiment. Thus, it is possible to measure brain waves, the eye electric signal and the myoelectric signal. The eye electric signal is the EOG (electrooculogram) for REM sleep observations whereas the myoelectric signal is the EMG (electromyography) of the chin muscle.

On top of that, in the first, second or third embodiment explained before, an infrared ray sensor can be provided on the reference electrode 3, the reference electrode 53 or the reference electrode 72 respectively. With such an infrared ray sensor, beats of the medical examinee can also be measured at the same time.

In addition, in the first, second or third embodiment explained before, the reference electrode 3, the reference electrode 53 or the reference electrode 72 respectively is employed as a reference electrode. It is to be noted, however, that implementations are by no means limited to the first, second and third embodiments. That is to say, it is possible to design a reference electrode into any of a variety of configurations which are different from the reference electrode 3, the reference electrode 53 and the reference electrode 72.

On top of that, in the first or third embodiment explained before, respectively the detection electrode 6 or the detection electrode 73 is employed as a detection electrode whereas in the second embodiment explained before, each of the first detection electrode 54 and the second detection electrode 55 is employed as a detection electrode. It is to be noted, however, that implementations are by no means limited to the first, second and third embodiments. That is to say, it is possible to design a detection electrode into any of a variety of configurations which are different from the detection electrode 6, the detection-electrode pair consisting of first detection electrode 54 and the second detection electrode 55 as well as the detection electrode 73.

In addition, in the first embodiment explained before, the main spring rod 5 is employed as a support body, in the second embodiment explained before, the support plate 52 and the signal wire 53E are employed as a support body whereas, in the third embodiment explained before, the electrode pressing section 74 and the signal wire 72A are employed as a support body. It is to be noted, however, that implementations are by no means limited to the first, second and third embodiments. That is to say, it is possible to design a support body into any of a variety of configurations which are different from the main spring rod 5, the support plate 52 and the signal wire 53E as well as the electrode pressing section 74 and the signal wire 72A.

The present application can be applied to a variety of fields such as fields in the medical industry and the game industry.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. An auricle-installed device comprising:
    a support body for supporting a reference electrode and a detection electrode, the support body comprising:
        a main section formed to fit a base of an auricle and provided with the reference electrode on one end of said main section; and
        a flexible wire-shaped member for connecting said main section to said detection electrode; and
    wherein the detection electrode has a structure that can be held in a hollow between the crus of helix of said auricle and the superior crux of antihelix of said auricle, and the reference electrode has a structure including:
        a substantially circular electrode plate configured to contact an ear lobe,
        a clip configured to connect the electrode plate to the one end of the support body, and
        a link section configured to enable the electrode plate to pivot about an end of the clip such that a user can secure the reference electrode to the ear lobe by pivoting the electrode plate about the link section toward the one end of the support body.

2. A bio-signal measurement apparatus comprising an auricle-installed device including:
    a support body for supporting a reference electrode and a detection electrode, the support body comprising:
        a main section formed to fit a base of an auricle and provided with the reference electrode on one end of said main section;
        a flexible wire-shaped member for connecting said main section to said detection electrode; and
        a differential amplifier configured to amplify a difference in electric potential between the reference electrode and the detection electrode as a bio-signal, and
    wherein the detection electrode has a structure that can be held in a hollow between the crus of helix of said auricle and the superior crux of antihelix of said auricle, and
    the reference electrode has a structure including:
        a substantially circular electrode plate configured to contact an ear lobe,
        a clip configured to connect the electrode plate to the one end of the support body, and
        a link section configured to enable the electrode plate to pivot about an end of the clip such that a user can secure the reference electrode to the ear lobe by pivoting the electrode plate about the link section toward the one end of the support body.

* * * * *